(12) United States Patent  
Semersky et al.

(10) Patent No.: US 8,327,688 B2
(45) Date of Patent: Dec. 11, 2012

(54) GAS PERMEATION TESTING SYSTEM

(75) Inventors: Frank E. Semersky, Holland, OH (US); Jonathan A. McGurk, Toledo, OH (US); Aaron R. Teitlebaum, Toledo, OH (US)

(73) Assignee: Plastic Technologies, Inc., Holland, OH (US)

( * ) Notice: Subject to any disclaimer, the term of this patent is extended or adjusted under 35 U.S.C. 154(b) by 332 days.

(21) Appl. No.: 12/669,122

(22) PCT Filed: Jul. 18, 2008

(86) PCT No.: PCT/US2008/070443
§ 371 (c)(1),
(2), (4) Date: Jan. 14, 2010

(87) PCT Pub. No.: WO2009/012437
PCT Pub. Date: Jan. 22, 2009

(65) Prior Publication Data
US 2010/0192668 A1   Aug. 5, 2010

Related U.S. Application Data

(60) Provisional application No. 60/950,697, filed on Jul. 19, 2007.

(51) Int. Cl.
*G01N 18/08* (2006.01)
*G01M 3/00* (2006.01)
(52) U.S. Cl. ............................................. 73/38; 73/49.2
(58) Field of Classification Search .............. 73/38, 49.2
See application file for complete search history.

(56) References Cited

U.S. PATENT DOCUMENTS

| | | | |
|---|---|---|---|
| 3,248,930 A | | 5/1966 | Speegle et al. |
| 3,348,395 A | | 10/1967 | Or, Jr. et al. |
| 3,494,175 A | | 2/1970 | Cusick et al. |
| 3,590,634 A | | 7/1971 | Pasternak et al. |
| 3,604,246 A | * | 9/1971 | Toren ................. 73/38 |
| 3,729,983 A | | 5/1973 | Coppens |
| 3,751,973 A | | 8/1973 | Strauss et al. |
| 3,805,593 A | | 4/1974 | Sandoz et al. |
| 3,805,594 A | | 4/1974 | Hayashi |
| 3,850,040 A | | 11/1974 | Orr, Jr. et al. |
| 4,364,261 A | * | 12/1982 | Askwith et al. .......... 73/40 |
| 4,459,893 A | | 7/1984 | Kitamura |
| 4,511,044 A | | 4/1985 | Connor et al. |
| 4,550,590 A | | 11/1985 | Kesson |
| 4,715,214 A | * | 12/1987 | Tveter et al. .......... 73/49.2 |
| 4,747,298 A | | 5/1988 | McDaniel |
| 4,788,850 A | | 12/1988 | Buschor et al. |
| 4,914,810 A | | 4/1990 | Zohler |
| 4,942,758 A | * | 7/1990 | Cofield ................ 73/49.2 |
| 5,001,935 A | | 3/1991 | Tekkanat et al. |
| 5,265,463 A | * | 11/1993 | Loebig ................ 73/38 |

(Continued)

FOREIGN PATENT DOCUMENTS
FR   2 308 100   11/1976

(Continued)

*Primary Examiner* — John Fitzgerald
(74) *Attorney, Agent, or Firm* — Fraser Clemens Martin & Miller LLC; J. Douglas Miller

(57) ABSTRACT

A system for the automated regulation of a gas permeation testing system is disclosed, wherein a control system in communication with a data processor facilitates more precise control of a pressurized fluid caused to flow through the gas permeation testing system.

17 Claims, 6 Drawing Sheets

U.S. PATENT DOCUMENTS

| | | | | |
|---|---|---|---|---|
| 5,367,797 A | * | 11/1994 | Zaim | 73/49.2 |
| 5,540,083 A | * | 7/1996 | Sato et al. | 73/40 |
| 6,013,026 A | | 1/2000 | Krauter et al. | |
| 6,327,898 B1 | * | 12/2001 | Harris | 73/49.2 |
| 6,347,545 B1 | * | 2/2002 | Osborn et al. | 73/49.2 |
| 6,591,661 B2 | | 7/2003 | Davey | |
| 6,598,463 B2 | | 7/2003 | Sharp et al. | |
| 6,817,238 B2 | | 11/2004 | Go Boncan et al. | |
| 6,857,307 B2 | * | 2/2005 | Gebele et al. | 73/38 |
| 6,952,945 B2 | | 10/2005 | O'Brien | |
| 6,964,191 B1 | | 11/2005 | Tata | |
| 7,266,993 B2 | * | 9/2007 | Strand et al. | 73/49.2 |
| 7,290,440 B2 | * | 11/2007 | Gocho | 73/49.2 |
| 7,543,479 B2 | * | 6/2009 | Thomas et al. | 73/37 |
| 7,555,934 B2 | * | 7/2009 | DeRoos et al. | 73/38 |
| 7,752,888 B2 | * | 7/2010 | Bogstad et al. | 73/38 |
| 7,805,982 B2 | * | 10/2010 | Hilab | 73/38 |
| 2004/0040372 A1 | | 3/2004 | Plester et al. | |
| 2005/0092071 A1 | * | 5/2005 | Lehmann | 73/52 |
| 2005/0268700 A1 | * | 12/2005 | Strand et al. | 73/49.2 |
| 2007/0215046 A1 | | 9/2007 | Lupke et al. | |

FOREIGN PATENT DOCUMENTS

| | | |
|---|---|---|
| JP | 10267826 | 10/1998 |
| JP | 2002 310843 A | 10/2002 |
| JP | 2004 279281 A | 10/2004 |
| WO | WO 01/48452 A2 | 7/2001 |
| WO | WO 2005/052555 A1 | 6/2005 |
| WO | WO 2007/077335 A1 | 7/2007 |

* cited by examiner

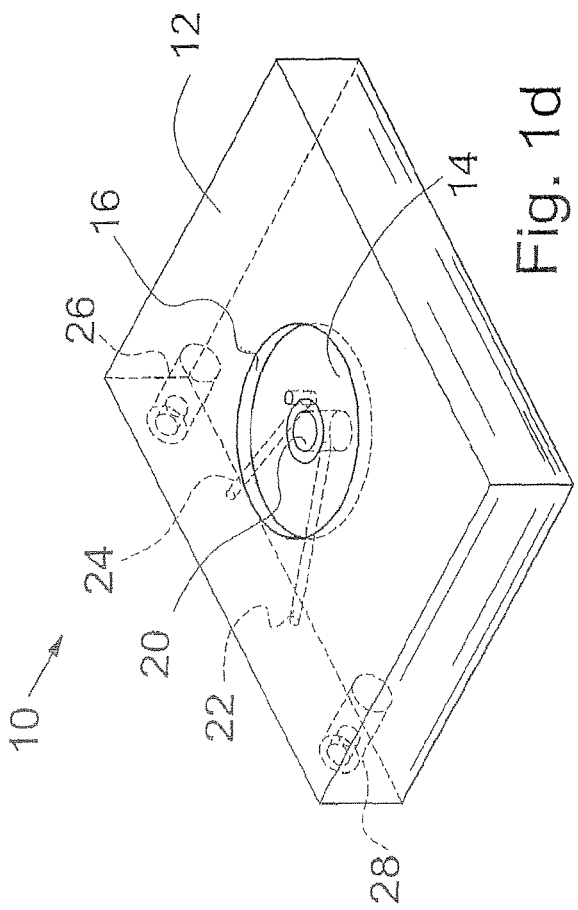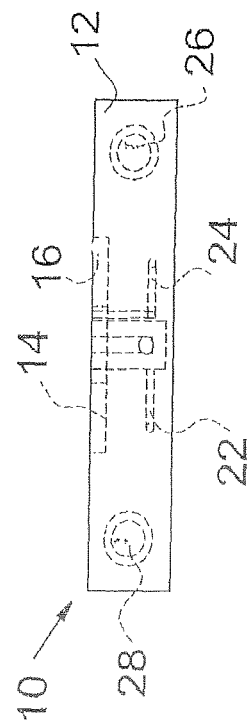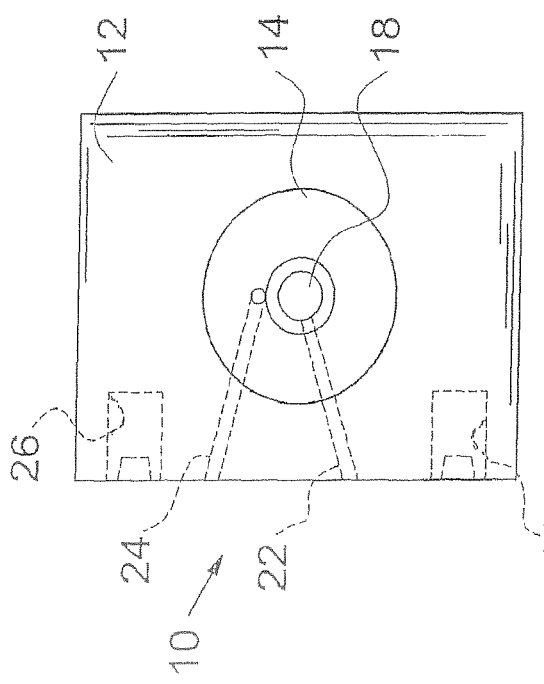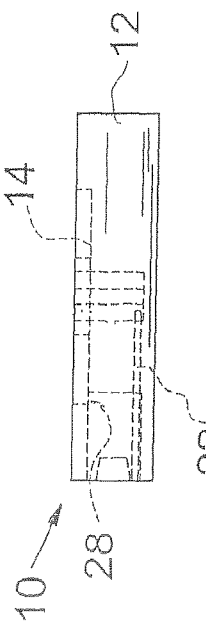

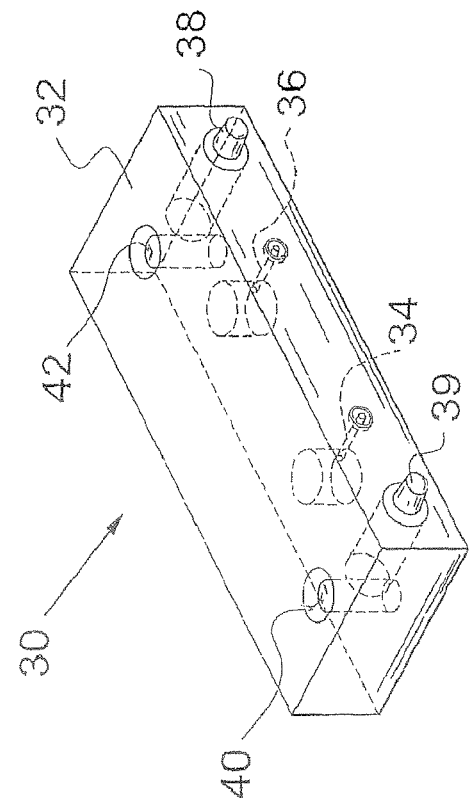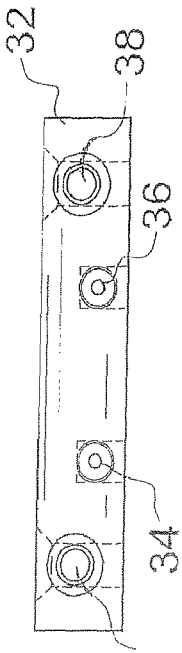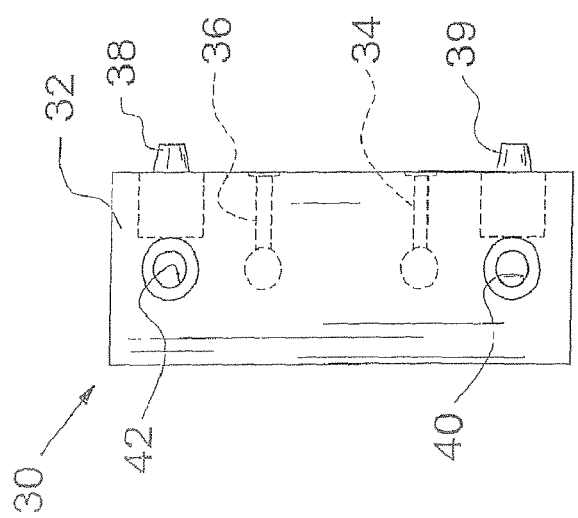

GAS PERMEATION TESTING SYSTEM

CROSS-REFERENCE TO RELATED APPLICATION

This application claims the benefit of U.S. Provisional Patent Application Ser. No. 60/950,697 filed on Jul. 19, 2007 hereby incorporated herein by reference.

FIELD OF THE INVENTION

The present invention relates to a container testing apparatus, and, more particularly, to a system and method for measuring the permeation of a gas through the walls of a container.

BACKGROUND OF THE INVENTION

In the preservation of beverages which are liable to be affected by oxidation, there is a problem that the beverages are oxidized by a small amount of oxygen present in a container used for storage. Therefore, it is of paramount importance to ascertain the oxygen permeation characteristics of the plastic containers to be used for the beverage storage. In the prior art, the systems for testing oxygen permeation require that each time a container is placed on or removed from a system for gas permeation testing, the containers to be tested must be affixed onto flat plates which have soldered connections that must be screwed onto a mating fitting of an associated manifold. Frequently, testing errors result, primarily from minute leakage around the fittings and components. Problems further increase with repeated use of the fittings.

One solution is to replace the fittings more often and to more meticulously affix the container to the flat plates to ensure a better connection. However, these options significantly increase the amount of time between testing of containers while still allowing for testing errors.

Furthermore, current operation of gas permeation test systems may require a user to manually manipulate the flow rate and pressure of a carrier gas into the container. Manual manipulation of the carrier gas flow rate and pressure results in imprecise control of the carrier gas within the system, thereby resulting in testing errors. Imprecise control of carrier gas flow rate and pressure also results in wear to the components of the system, thereby reducing the useful life thereof.

Those skilled in the art have continued to search for the solution of how to provide a practical testing system.

SUMMARY OF THE INVENTION

Concordant and congruous with the present invention a system for automated regulation of the gas permeation test system with a control system to facilitate more precise control of test conditions, has surprisingly been discovered.

In one embodiment of the invention, a gas permeation test system 110 for measuring the permeation of a gas through a container comprises a gas permeation test system in fluid communication with a source of pressurized fluid adapted to generate a feedback signal representing at least one measured characteristic; and a control system in communication with the gas permeation test system adapted generate a control signal to adjust operation of the gas permeation test system in response to the feedback signal.

In another embodiment, a gas permeation test system 110 for measuring the permeation of a gas through a container comprises a test system in fluid communication with a source of pressurized fluid adapted to generate a feedback signal representing one of a measured characteristic of a fluid; a means for regulating a flow of the fluid; and a control system in communication with the gas permeation test system adapted to generate a control signal to adjust operation of the gas permeation test system in response to the feedback signal.

In another embodiment, a method of controlling the gas permeation testing of blow molded containers includes the steps of: providing a gas permeation test system; securing a container to the gas permeation test system; measuring a characteristic of a pressurized fluid caused to flow through the gas permeation test system and container and generating a feedback signal representing the measured characteristic; and adjusting operation of the gas permeation test system in response to the feedback signal to effect the desired change to the pressurized fluid caused to flow through the gas permeation test system.

Further objects and advantages of the invention will be apparent from the following description and appended claims, reference being made to the accompanying drawings forming a part of the specification.

BRIEF DESCRIPTION OF THE DRAWINGS

Other objects and advantages of the invention will become readily apparent to those skilled in the art from reading the following description of the invention when considered in the light of the accompanying drawings, in which:

FIGS. 1a, 1b, 1c, and 1d are, respectively, top plan, end elevational, front elevational, and perspective views of a sample plate of a gas permeation testing system embodying features of the present invention;

FIGS. 2a, 2b, 2c, and 2d are, respectively, top plan, end elevational, front elevational, and perspective views of a manifold of the gas permeation testing system embodying features of the present invention;

Figures 3A, 3B, 3C:
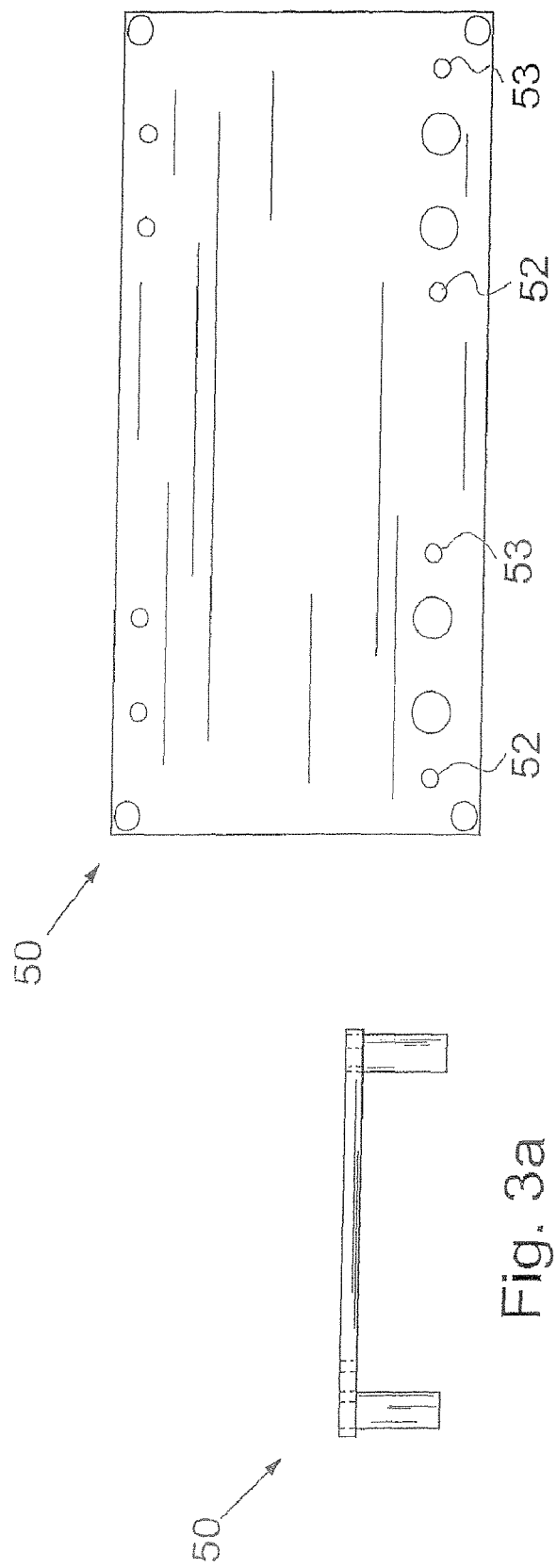
FIGS. 3a, 3b, and 3c are, respectively, end elevational, top plan, and front elevational views of a base plate of the gas permeation testing system embodying the features of the present invention.

It is to be understood that the present invention is not limited in its application to the details of construction and arrangement of components illustrated in the accompanying drawings, since the invention is capable of other embodiments, and of being practiced or carried out in various ways within the scope of the appended claims. Also, it is to be understood that the phraseology and terminology employed herein is for the purpose of description, and not of limitation.

DETAILED DESCRIPTION OF THE PREFERRED EMBODIMENT

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Referring to the accompanying drawings, there is shown components of a gas permeation testing system for mounting and connecting plastic material and a control system, such as used in containers for permeation testing which embody the features of the invention.

The gas permeation testing system includes two main components; namely, moveable sample plates to which a container to be tested is affixed; and an associated manifold system.

A sample plate, generally indicated by reference numeral 10, is shown in FIGS. 1a, 1b, 1c, and 1d is adapted to be capable to receive pins of an associated manifold 30 shown in FIGS. 2a, 2b, 2c, and 2d. The sample plate 10 and the manifold 30 are suitably affixed to a base plate 50 shown in FIGS. 3a, 3b, and 3c by suitable fasteners. The sample plate 10, the manifold 30, and the base plate 50 are assembled to form the gas permeation testing assembly 100 as shown in FIG. 4.

The sample plate 10 includes a main body 12 having an annular recess 14 for receiving the open end of the neck or finish of a plastic container to be tested. The recess 14 is defined by an annular shoulder 16. A coaxial recess 18 is formed centrally of the annular shoulder 16. The open end of the recess 18 is defined by an upstanding annular ring 20. A conduit 22 is formed in the main body 12 to provide communication between a remote source of pressure fluid and the interior of the container being tested.

A similar conduit 24 is formed in spaced relation therefrom in the main body 12 to provide communication with a return of the pressure fluid introduced through the conduit 22. Spaced apart bushings 26 and 28 are formed to extend inwardly of the main body 12 and receive cooperating locating pins, as will be explained hereinafter.

FIGS. 2a, 2b, 2c, and 2d illustrate a manifold, generally indicated by reference numeral 30, includes a main body 32 having a conduit 34 to communicate with the inlet of the sample plate conduit 22; and a conduit 36 to communicate with the sample plate conduit 24. Coupling means including spaced apart pins 38 and 39 are provided to selectively couple the sample plate 10 and the manifold 30.

Grooves may be circumscribed around the inlets and outlets of conduits of the sample plate 10 and the manifold 30 to receive o-ring seals, for example. The seals are utilized to provide fluid-tight system when the sample plate 10 is in operative position.

Any suitable means of selectively coupling the sample plate 10 and manifold 30 may be used. It has been found that satisfactory results may be achieved by utilizing the spaced apart inwardly extending bushing 26 and 28 in the sample plate 10 which receive the respective pins 38 and 39 of the manifold 30. Manifold mold-style pins 38 and 39 ensure proper alignment with sample plate mold-style bushings 26 and 28.

Figure 4:
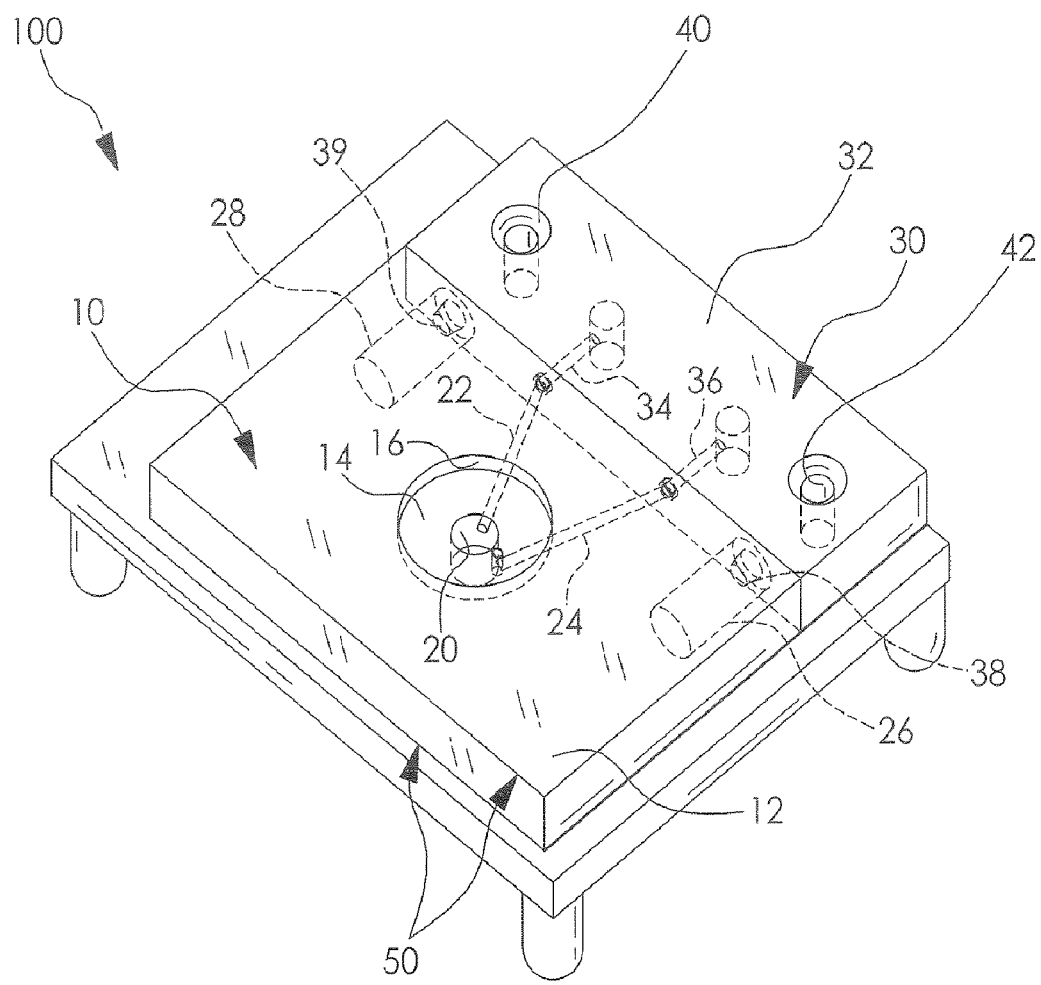
FIG. 4 is a perspective view of the gas permeation testing system embodying the features of the present invention.

The manifold 30 can be mounted to a base plate, generally referred to by reference numeral 50 illustrated in FIGS. 3a, 3b, and 3c. The base plate 50 serves as a support for the sample plate 10 and the manifold 30. The manifold 30 is provided with spaced apart passageways or holes 40 and 42 to receive suitable threaded fasteners. The threaded fasteners are received within internally threaded holes 52 and 53, respectively, of the base plate 50 to assure proper alignment. A pair of spaced apart passageways or holes is formed in the base plate 50 to allow the passage of conduits communicating with the manifold conduits 34, 36. In the embodiment illustrated, the base plate 50 is adapted to accommodate a pair of manifolds 30.

Once aligned, the sample plate 10 is connected with the manifold 30. The connection may be tightened to urge the sample plate 10 against o-rings in the manifold 30. Compression of the sample plate 10 against the o-rings results in a fluid-tight conduit-container-manifold system.

The sample plate 10, manifold 30, and base plate 50 are preferably constructed of aluminum or other lightweight durable alloy. Lightweight components are desired for easier portability of system components and allow rapid exchange of sample plates during testing. However, the components of the system may be constructed of any appropriate material that withstand system temperature, pressure, and use requirements.

The testing of a container typically involves the following steps. First, the open side of a container to be tested is placed in the recess 14 and secured to the sample plate 10 with an epoxy resin or other suitable adhesive material. The sample plate 10 is then selectively coupled to the manifold 30 which has been attached to the base plate 50. The sample plate 10 is securely compressed against the o-rings received within the conduits of the manifold 30 to close the system. Compression occurs by tightening the connection between the sample plate 10 and the manifold 30 by any means, such as by clamping, for example.

After the system has been closed, the pressure fluid is allowed to flow into the container being tested through the manifold conduit 34 and the sample plate conduit 22. Favorable results have been found wherein the pressure fluid is pure nitrogen. As the pressure fluid is introduced into the container, it flows out of the container through the sample plate conduit 24 and the manifold conduit 36. Any gas which permeated through the container during the test, will also flow out of the container through the sample plate conduit 24 and the manifold conduit 36 to the testing sensor.

A system described above for testing the permeation characteristics of a container may also be used to test permeation characteristics of a film, for example. A film may be disposed on an open-ended container and sealed or otherwise connected to the container so the flow of fluid around the film into the container is militated against. The sample plate conduits 22, 24 described herein are in communication with the container. The pressure fluid is introduced into the container and exposed to the inner side of the film. The outer side of the film is exposed to atmosphere or a controlled environment. Gas which permeates through the film is picked up by the pressure fluid and tested to determine the permeation characteristics of the film.

Figure 5:
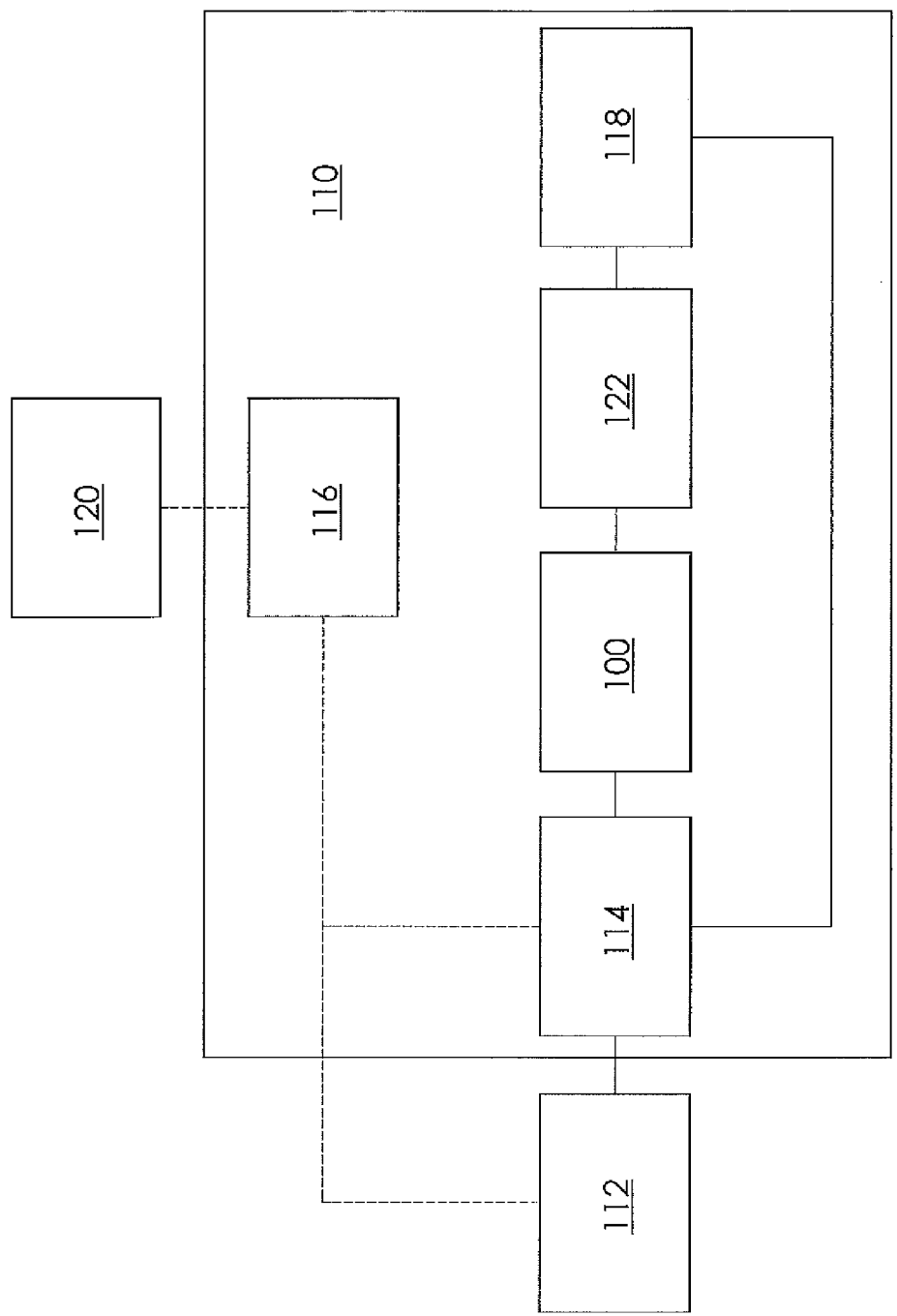
FIG. 5 is a schematic block diagram of a gas permeation testing system 110 according to the present invention incorporating the components illustrated in FIGS. 1-3.
Figure 6:
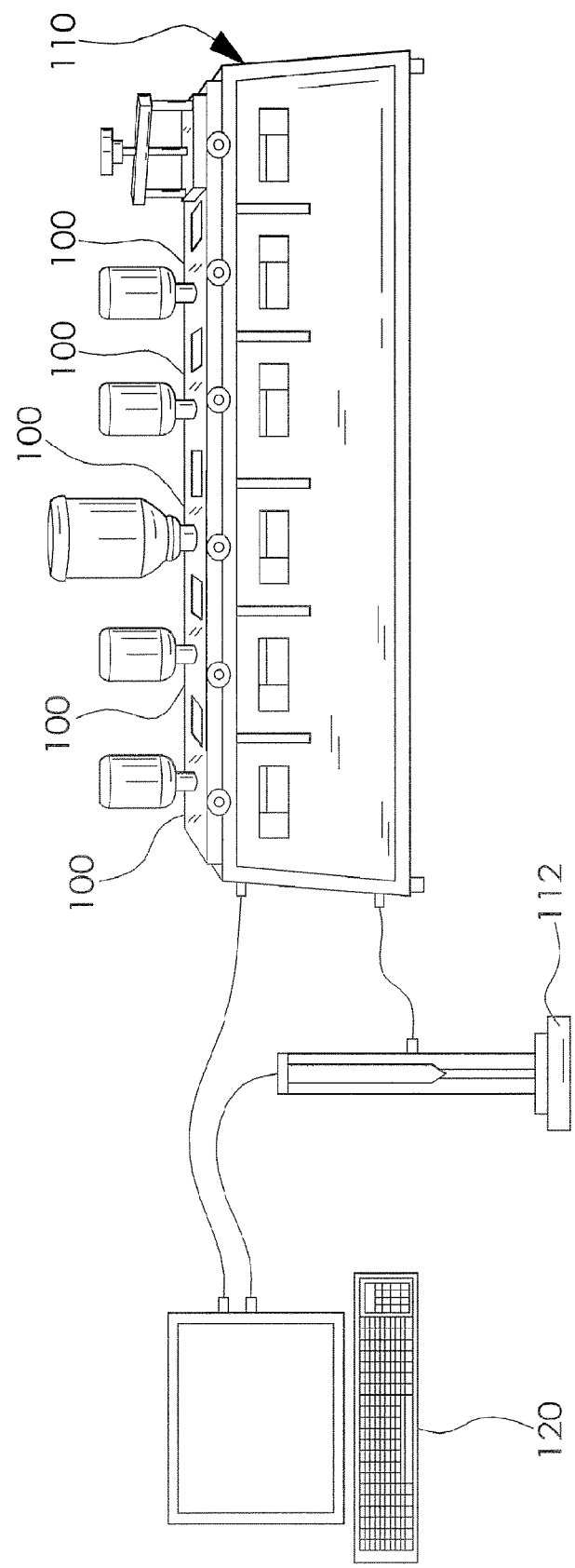
FIG. 6 is a view of a gas permeation testing system 110 according to the present invention incorporating the components illustrated in FIGS. 1-3.

FIGS. 5 and 6 illustrate a gas permeation testing system 110 including a plurality of gas permeation testing apparatus 100 as shown in FIGS. 1-4 and described herein and having at least one oxygen sensor 122 and at least one sample presence detector. A control system 116 in electrical communication with the gas permeation testing system 110 is adapted to detect or measure at least one of the following: the flow of the pressurized fluid into a container disposed on the gas permeation testing system 110; the presence of the pressurized fluid in the system 110; the pressure of the pressurized fluid in the system 110; the temperature of the pressurized fluid; and the presence of a leak of the fluid from the system 110. The control system 116 is further adapted to generate a feedback signal based on at least one of the measured characteristics. An unexpected loss in the pressure of the fluid in the system 110 may indicate a leak in the system 110 or a lack of fluid from a fluid source. Electrical connections are indicated by dashed lines in FIG. 5. The control system 116 is further in communication with a data processor adapted to receive and interpret data. As shown in FIGS. 5 and 6, the data processor is a computer 120 including software adapted to receive and interpret the feedback signal from the gas permeation testing system 110.

The gas permeation testing system 110 is installed downstream from a source of pressure fluid 112. A means for regulating 114 a flow of a pressure fluid stored in the source of pressure fluid 112 is disposed between the oxygen sensor 122 of the system 110 and the source of pressurized fluid 112. The means for regulating 114 is a three-way valve in fluid communication with the source of pressure fluid 112, the gas permeation testing system 110, and an exhaust system 118. The means for regulating 114 may be any valve, such as a solenoid valve or a gas pressure regulator, for example. The gas permeation testing system 110 may also include a pressure sensor, as desired. It is also understood that the system 110 may include any number of means for regulating 114, as desired.

The gas permeation testing system 110 is adapted to generate a feedback signal representing a measured or monitored characteristic of the fluid caused to flow through the system 110 and/or the presence of a sample. The feedback signal is received by the control system 116 and the control system 116 generates a control signal which is sent to the flow regulator 114, the source of pressure fluid 112, the gas permeation testing system 110, and/or any other component of the system 110, as desired, to facilitate adjustment and feedback control of the system 110. System changes may include a change in the characteristics of the pressurized fluid flowing through the system 110, such as changes to the flow rate, the pressure, and the temperature of the fluid, for example. System changes may also include adjustment of the means for regulating 114 to militate against fluid flow to a particular system component. For example, fluid from the fluid source 112 may be caused to flow through the gas permeation testing system 110, past the oxygen sensor 122 for detection and measurement, and then to the exhaust system 118. However, if the sample presence detector sends a feedback signal to the control system 116 and/or the computer 120 indicating the lack of a sample, the control system 116 will review the feedback signal and direct a control signal to a desired component. If the feedback signal is also sent to the computer 120 for interpretation, the software of the computer will review the feedback signal and direct the control signal 116 to direct a control signal to a desired component. If a sample is not present, the control signal will be sent to the means for regulating 114 to cause an adjustment thereto to facilitate the bypass of the fluid from the gas permeation system 110 to the exhaust system 118 without flowing past the oxygen sensor 122. The control system 116 or the computer 120 may also cause an adjustment to the means for regulating 114 in the event of a pressure drop in the gas permeation testing system 110 to cause the fluid to bypass the oxygen sensor 122. By bypassing the fluid around the oxygen sensor 122, the oxygen sensor 122 may be isolated to militate against exposure of the oxygen sensor 122 to oxygen to extend a useful life thereof.

Additionally, before the measurement of a new sample, the gas permeation testing system 110 and the means for regulating 114 may be configured to facilitate a bypass of the fluid around the oxygen sensor 122 to purge the gas permeation testing system 110 and/or a testing apparatus 100. Once the purge operation is complete, the gas permeation testing system 110 and the means for regulating 114 may be configured to facilitate a flow of the fluid past the oxygen sensor 122 for measurement and the testing of a sample.

The gas permeation testing system 110 may include a plurality means for regulating such as a three-way valve and a two-way valve. The plurality of means for regulating may by driven together to facilitate adjustment thereof in concert. The plurality of means for regulating is in electrical communication with the controller 116 which is in electrical communication with the computer 120. In a first position, the plurality of means for regulating facilitates the flow of fluid through the sample, past the oxygen sensor 122 for measurement, and then to the exhaust system 118. In a second position, the plurality of means for regulating facilitates the bypass of the fluid through the sample, around the oxygen sensor 122, and to the exhaust system 118.

Additionally, before the measurement of a new sample, the gas permeation testing system 110 and the means for regulating 114 may be configured to facilitate a bypass of the fluid around the oxygen sensor to purge the gas permeation testing system 110 and/or a testing apparatus 100. Once the purge operation is complete, the gas permeation testing system 110 and the means for regulating 114 may be configured to facilitate a flow of the fluid past the oxygen sensor for measurement and the testing of a sample.

The gas permeation testing system 110 may include a plurality means for regulating such as a three-way valve and a two-way valve. The plurality of means for regulating may by driven together to facilitate adjustment thereof in concert. The plurality of means for regulating is in electrical communication with the controller 116 which is in electrical communication with the computer 120. In a first position, the plurality of means for regulating facilitates the flow of fluid through the sample, past the oxygen sensor for measurement, and then to the exhaust system 118. In a second position, the plurality of means for regulating facilitates the bypass of the fluid through the sample, around the oxygen sensor, and to the exhaust system 118.

Information related to the feedback signal obtained by the control system 116, as well as any adjustments made to the system 110 by the control system 116, may be displayed to an operator on a display device of the computer 120 for real time data and data trend analysis. An alarm signal may also be sent to the computer 120 from the control system 116 or from the computer 120 to alert an attendant of an event requiring corrective action. For example, in the event of a leak of the fluid from the system 110, the gas permeation testing system 110 may send a feedback signal to the control system 116 to trigger an alarm signal to be sent to the computer 120. Once the attendant is notified of the event or alarm, the system 110 may be adjusted or shut-down for repair.

The feedback control according to the present invention will generate the required recommended process control functions. These controls will allow for better process monitoring, less need for labor to intervene in the process, more precise control of the pressurized fluid in the system 110, militate against process error, and militate against wear on the components of the system 110 contacted by the pressurized fluid.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A gas permeation testing system for measuring the permeation of a gas through a sample comprising:
   a sample plate adapted to receive a sample to be tested;
   a source of pressurized fluid in fluid communication with the sample plate;
   measuring means in communication with at least one of said sample plate and said source of pressurized fluid and adapted to measure at least one characteristic of the sample and the pressurized fluid and adapted to generate a feedback signal representing the measured characteristic, wherein the measuring means includes an oxygen sensor; and a control system in communication with at least one of said source of pressurized fluid, said sample plate adapted to generate a control signal in response to the feedback signal, the control signal causing an adjustment of said source of pressurized fluid, wherein the control system is in communication with the oxygen sensor and the control system is configured to selectively cause the fluid to bypass the oxygen sensor.

2. The gas permeation testing system of claim 1, wherein the sample is one of a plastic container and a film.

3. The gas permeation testing system of claim 1, wherein the measured characteristic is at least one of an amount of gas permeation through a container, a fluid flow rate, a fluid pressure, a fluid temperature, and a sample presence.

4. The gas permeation testing system of claim 1, wherein said measuring means is adapted to detect a leak of the fluid from the gas permeation testing system.

5. The gas permeation testing system of claim 1, further including a plurality of sample plates in communication with said control system.

6. The gas permeation testing system of claim 1, further including a means for regulating a flow of the fluid in communication with said control system.

7. The gas permeation testing system of claim 6, wherein said control system is in communication with said means for regulating a flow of the fluid.

8. The gas permeation testing system of claim 1, further including a data processor in communication with said control system.

9. The gas permeation testing system of claim 8, wherein said data processor includes software adapted to receive and interpret data from said control system.

10. The gas permeation testing system of claim 8, wherein said data processor includes a display device adapted to display information regarding at least one of the measured characteristic and the adjustments made by said control system.

11. The gas permeation testing system of claim 8, wherein one of said control system and said data processor is adapted to generate an alarm signal.

12. The gas permeation testing system of claim 11, wherein said display device is adapted to generate an alarm responsive to the alarm signal.

13. A gas permeation testing system for measuring the permeation of a gas through a container comprising:
a sample plate adapted to receive a container to be tested;
a source of pressurized fluid in fluid communication with an interior of the container;
measuring means in communication with at least one of said sample plate and said source of pressurized fluid and adapted to measure at least one characteristic of the sample and the pressurized fluid and adapted to generate a feedback signal representing the measured characteristic, wherein the measuring means includes an oxygen sensor;
a control system in communication with at least one of said source of pressurized fluid, said sample plate adapted to generate a control signal in response to the feedback signal, the control signal causing an adjustment of said source of pressurized fluid, wherein the control system is in communication with the oxygen sensor and the control system is configured to selectively cause the fluid to bypass the oxygen sensor; and
a means for regulating a flow of the fluid in communication with said control system and said source of pressurized fluid.

14. The gas permeation testing system of claim 13, wherein the measured characteristic is at least one of an amount of gas permeation through a container, a fluid flow rate, a fluid temperature, and a container presence.

15. The gas permeation testing system of claim 13, wherein said measuring means is adapted to detect a leak of the fluid from the gas permeation testing system.

16. A method of controlling a gas permeation testing system including the steps of:
providing a sample plate adapted to receive a sample to be tested;
providing a source of pressurized fluid in communication with the sample;
providing a measuring means in communication with at least one of the sample plate and the source of pressurized fluid adapted to generate a feedback signal representing a measured characteristic, wherein the measuring means includes an oxygen sensor;
providing a control system in communication with at least one of the source of pressurized fluid adapted to generate a control signal in response to the feedback signal, wherein the control system is in communication with the oxygen sensor and the control system is configured to selectively cause the fluid to bypass the oxygen sensor;
securing the sample to the sample plate;
causing the fluid to flow from the source of pressurized fluid to at least the sample;
measuring at least one characteristic of the sample or the fluid to generate the feedback signal;
generating the control signal in response to the feedback signal; and
selectively adjusting one of the sample plate and the source of pressurized fluid responsive to the control signal to effect a desired change to the source of pressurized fluid or the sample.

17. The method of claim 16, wherein the measuring means is adapted to detect a leak of the fluid from the gas permeation testing system.

* * * * *